United States Patent
Zarsky et al.

(10) Patent No.: US 9,867,996 B2
(45) Date of Patent: Jan. 16, 2018

(54) METHODS AND SYSTEMS FOR SKIN TREATMENT

(71) Applicant: BTL Holdings Limited, Limassol (CY)

(72) Inventors: Jan Zarsky, Framington, MA (US); Tomáš Schwarz, Prague (CZ)

(73) Assignee: BTL Holdings Limited, Limassol (CY)

(*) Notice: Subject to any disclaimer, the term of this patent is extended or adjusted under 35 U.S.C. 154(b) by 917 days.

(21) Appl. No.: 14/278,756

(22) Filed: May 15, 2014

(65) Prior Publication Data

US 2014/0249609 A1    Sep. 4, 2014

Related U.S. Application Data (63) Continuation-in-part of application No. 13/297,934, filed on Nov. 16, 2011, now abandoned, and a continuation-in-part of application No. PCT/US2012/064942, filed on Nov. 14, 2012, which is a continuation-in-part of application No.
(Continued)

(51) Int. Cl.

| | |
|---|---|
| *A61F 7/00* | (2006.01) |
| *A61N 1/40* | (2006.01) |
| *A61N 5/02* | (2006.01) |
| *A61B 18/18* | (2006.01) |
| *A61B 18/00* | (2006.01) |
| *A61B 18/14* | (2006.01) |
| *A61N 5/00* | (2006.01) |

(52) U.S. Cl.
CPC .......... *A61N 1/403* (2013.01); *A61B 18/1815* (2013.01); *A61N 1/40* (2013.01); *A61N 5/025* (2013.01); *A61B 2018/00464* (2013.01); *A61B 2018/00791* (2013.01); *A61B 2018/147* (2013.01); *A61N 2005/007* (2013.01)

(58) Field of Classification Search
None
See application file for complete search history.

(56) References Cited

U.S. PATENT DOCUMENTS

| | | |
|---|---|---|
| 866,376 A | 9/1907 | Meade |
| 3,854,968 A | 12/1974 | Minnick |
| | (Continued) | |

FOREIGN PATENT DOCUMENTS

| | | |
|---|---|---|
| CN | 1000998519 A | 7/2007 |
| EP | 1158919 A1 | 12/2001 |
| | (Continued) | |

OTHER PUBLICATIONS

Korean Patent Office, Notice of Preliminary Rejection issued in KR Patent Application No. 10-2014-7015830 (dated Apr. 20, 2015).
(Continued)

*Primary Examiner* — Kaitlyn Smith
(74) *Attorney, Agent, or Firm* — Kenneth H. Ohriner; Perkins Coie LLP (57) ABSTRACT

Systems and methods are provided for focused remodeling and downsizing the volume of subcutaneous lipid-rich cells, body contouring, and tightening skin tissue, using controlled heating of the targeted areas on the body. Electromagnetic energy heats skin layers or tissues to achieve an aesthetic effect. The electromagnetic energy may be applied via an applicator without touching the skin. A spacer of insulating or dielectric material may be provided between the applicator and the skin.

18 Claims, 6 Drawing Sheets

Related U.S. Application Data

13/297,608, filed on Nov. 16, 2011, now Pat. No. 8,548,599, and a continuation-in-part of application No. 13/297,934, filed on Nov. 16, 2011, now abandoned.

(56) References Cited

U.S. PATENT DOCUMENTS

| | | | |
|---|---|---|---|
| 4,255,398 A | 3/1981 | Tanaka | |
| 4,256,500 A | 3/1981 | Turpin, Jr. | |
| 4,256,504 A | 3/1981 | Dunstan, Jr. | |
| 5,118,219 A | 6/1992 | Walker, Jr. | |
| 5,295,955 A | 3/1994 | Rosen | |
| 5,507,790 A * | 4/1996 | Weiss | A61F 7/00 128/897 |
| 5,660,836 A | 8/1997 | Knowlton | |
| 5,755,753 A * | 5/1998 | Knowlton | A61B 18/12 606/33 |
| 5,778,894 A | 7/1998 | Dorogi et al. | |
| 5,919,219 A | 7/1999 | Knowlton | |
| 5,948,011 A * | 9/1999 | Knowlton | A61B 18/12 606/33 |
| 6,047,215 A * | 4/2000 | McClure | A61B 18/1492 607/101 |
| 6,208,903 B1 | 3/2001 | Richards | |
| 6,241,753 B1 | 6/2001 | Knowlton | |
| 6,334,074 B1 | 12/2001 | Spertell | |
| 6,377,855 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,406,474 B1 | 6/2002 | Neuberger et al. | |
| 6,413,255 B1 * | 7/2002 | Stern | A61B 18/14 606/41 |
| 6,511,475 B1 | 1/2003 | Altshuler et al. | |
| 6,641,658 B1 | 11/2003 | Dubey | |
| 6,662,054 B2 | 12/2003 | Kreindel et al. | |
| 6,749,624 B2 | 6/2004 | Knowlton | |
| 6,766,202 B2 | 7/2004 | Underwood et al. | |
| 7,006,874 B2 | 2/2006 | Knowlton et al. | |
| 7,189,230 B2 | 3/2007 | Knowlton | |
| 7,229,346 B1 | 6/2007 | Stern et al. | |
| 7,229,436 B2 * | 6/2007 | Stern | A45D 44/22 606/41 |
| 7,267,675 B2 | 9/2007 | Stern et al. | |
| 7,630,774 B2 | 12/2009 | Karni et al. | |
| 7,643,883 B2 | 1/2010 | Kreindel | |
| 9,446,258 B1 * | 9/2016 | Schwarz | A61N 1/403 |
| 2003/0187488 A1 | 10/2003 | Kreindel et al. | |
| 2004/0003757 A1 | 1/2004 | Chern Lin et al. | |
| 2004/0040474 A1 | 3/2004 | Perez-Pena et al. | |
| 2005/0182462 A1 | 8/2005 | Chornenky et al. | |
| 2006/0036300 A1 | 2/2006 | Kreindel | |
| 2006/0173518 A1 | 8/2006 | Kreindel | |
| 2006/0265034 A1 | 11/2006 | Aknine et al. | |
| 2007/0038206 A1 | 2/2007 | Altshuler et al. | |
| 2007/0106349 A1 * | 5/2007 | Karni | A61B 18/042 607/101 |
| 2007/0282318 A1 | 12/2007 | Spooner et al. | |
| 2008/0183251 A1 | 7/2008 | Azar et al. | |
| 2009/0024193 A1 | 1/2009 | Altshuler et al. | |
| 2009/0125013 A1 | 5/2009 | Sypniewski et al. | |
| 2009/0221938 A1 | 9/2009 | Rosenberg et al. | |
| 2010/0016849 A1 * | 1/2010 | Rosenberg | A61B 18/14 606/33 |
| 2011/0060391 A1 | 3/2011 | Unetich et al. | |
| 2011/0112520 A1 | 5/2011 | Michael | |
| 2011/0295187 A1 | 12/2011 | Shanks et al. | |
| 2012/0010609 A1 | 1/2012 | Deem et al. | |
| 2012/0022622 A1 | 1/2012 | Johnson et al. | |
| 2012/0078141 A1 * | 3/2012 | Knowlton | A61B 18/14 601/3 |
| 2014/0200564 A1 * | 7/2014 | Schomacker | A61B 18/20 606/9 |

FOREIGN PATENT DOCUMENTS

| | | |
|---|---|---|
| GB | 2265916 | 10/1993 |
| WO | 97-39054 | 10/1997 |
| WO | 2000053113 | 9/2000 |

OTHER PUBLICATIONS

Korean Patent Office, Notice of Preliminary Rejection issued in KR Patent Application No. 10-2015-7009375 (dated Jun. 11, 2015).
Korean Patent Office, Notice of Preliminary Rejection issued in KR Patent Application No. 10-2014-7015830 (dated Aug. 19, 2015).
Korean Patent Office, Final Rejection issued in KR Patent Application No. 10-2015-7009375 (dated Dec. 18, 2015).
The State Intellectual Property Office of China, The First Office Action issued in CN Patent Application No. 201280055846.4 (dated Nov. 17, 2015).
European Patent Office, "Examination Report" issued in EP Patent Application No. 12 849 633.8 (dated Jan. 9, 2016).
Korean Patent Office, "Notice of Preliminary Rejection (English Translation)" issued in KR Patent Application No. 10-2015-7009375 (dated Jun. 11, 2015).
Korean Patent Office, "Third Party's Opposition Paper" with redacted summary, as filed in KR Patent Application No. 10-2016-7001474 (Jan. 16, 2017).
European Patent Office, extended European search report in EP Patent Application No. 12849633.8 dated Jun. 15, 2015.
Nel, P., et al., "Non-destructive micro-X-ray diffraction analysis of painted artefacts: Determination of detection limits for the chromium oxide-zinc oxide matris", Nuclear Instruments and Methods in Physics Research B, 251, pp. 489-495 (2006).
Abo-El-Enein, S.A., et al., "Blended Cements Containing Cement Kiln Dust", Silicates Industries, vol. 59, No. 9-10, pp. 265-269 (1994).
Hawkins, Peter et al., "The Use of Limestone in Portland Cement: A State-of-the-Art Review", Engineering Bulletin 227, Portland Cement Association, Skokie, Illinois, 41 pages (2003).
Ravindrarajah, R.S., "Use of cement kiln dust in concrete", The International Journal of Cement Composites and Lightweight Concrete, vol. 4, No. 2, pp. 95-102 (May 1982).
Kitahara,Shinichi et al., "Precision and detection limit of quality test for amorphous drug in powder x-ray diffractometry". International Journal of Pharmaceutics, 283, pp. 63-69 (2004).
Cody, A.M, et al., "The effects of chemical environment on the nucleation, growth, and stability of ettringite". Cement and Concrete Research, 34, pp. 869-881 (2004).

* cited by examiner

METHODS AND SYSTEMS FOR SKIN TREATMENT

PRIORITY CLAIM

This Application is a Continuation-in-Part of U.S. patent application Ser. No. 13/297,934 filed Nov. 16, 2011 and now pending. This Application is also a Continuation-in-Part of International Patent Application No. PCT/US2012/064942 filed Nov. 14, 2012 and now pending, which claims priority to U.S. patent application Ser. No. 13/297,608 filed Nov. 16, 2011, now U.S. Pat. No. 8,548,599, and U.S. patent application Ser. No. 13/297,934, filed Nov. 16, 2011, and now pending. Each of these Applications is incorporated herein by reference.

FIELD OF THE INVENTION

The field of the invention is non-invasive, non-traumatic skin treatment. Methods are provided for focused remodeling and downsizing subcutaneous lipid-rich cells, body contouring and skin tightening, and for treatment of stretch marks and cellulite. In particular, the invention relates to controlled heating of the targeted areas on the human body using electromagnetic waves.

BACKGROUND OF THE INVENTION

Human skin is composed of three basic elements: the epidermis, the dermis and the hypodermis or so called sub cutis. The dermis consists of collagen, elastic tissue and reticular fibers. The hypodermis is the lowest layer of skin and contains hair follicle roots, lymphatic vessels, collagen tissue, nerves and also subcutaneous fat forming an adipose fat tissue. Adipose fat tissue is formed by aggregation of fat cells containing stored lipid (fat). Most fat tissue accumulations result from lipids (fat) primarily from food, when energy intake derived from food exceeds daily energy needs. This may result in an increase in fat cell size or fat cell number or both. Mature fat cells are very large, ranging up to 120 microns in diameter and containing as much as 95% lipid (fat) by volume. The subcutaneous adipose tissue layer may be thin (about 1 cm or less) or in humans of slight or moderate body type.

Excess adipose tissue may be perceived as aesthetically undesirable. Dieting and exercise may result in reduction of adipose tissue and weight loss. However, foremost people, the reduction in adipose tissue volume occurs rather unpredictably from all anatomical areas. This can leave the areas intended for reduction, for example, the abdomen, largely unaffected, even after significant body weight loss. Various invasive and non-invasive methods have been developed to remove unwanted subcutaneous fat from specific areas of the body.

The main invasive method is surgical-assisted liposuction, where selected volumes of subcutaneous fat are mechanically aspirated out from the patient at desired anatomical sites of the body. However, liposuction procedures are invasive and can be painful and traumatic, with many undesirable side effects and risks. Lipodissolve is another invasive procedure involving a series of drug injections intended to dissolve and permanently remove small pockets of fat from various parts of the body. It also is known as mesotherapy, lipozap, lipotherapy, or injection lipolysis. Lipodissolve also has many disadvantages and risks, to the extent that various medical associations have issued health warnings against using it.

The non-invasive methods concentrate on the acceleration of the lipolysis as the natural process of the fat reduction. This can be achieved in several ways. One of them is application of pharmaceuticals accelerating the lipolysis. However, when applied topically they tend only to affect the outermost layers of the skin, rarely penetrating to the sub dermal vascular plexus. Another method uses radio frequency or ultrasound energy focused on adipose tissue to cause cell destruction and death. These methods tend to damage the melanocyte in the epidermis. The hyper thermic temperatures destroy the target tissues and leave the body to remove the dead cellular and other debris. Non-invasive heating techniques have also been used. These involve heating the adipose fat tissue to about 40° C. or more via direct contact with a heating element. These non-invasive methods have certain disadvantages as well, and have been used with varying degrees of success.

Accordingly, there is need for improved methods and systems for subcutaneous treatments. There is also a need to improve the energy flow through the skin of patient to reduce or eliminate risks of overheating the skin.

SUMMARY OF THE INVENTION

New methods have now been invented. A method for treating subcutaneous tissue includes positioning one or more applicators adjacent to the skin of a patient, but not touching the skin. Electromagnetic energy is transmitted from the applicators into the subcutaneous tissue. The subcutaneous tissue is heated via the electromagnetic energy. The subcutaneous tissue may be remodeled. The volume of lipid-rich cells in the subcutaneous tissue may be reduced via the healing. The electromagnetic waves may be applied in a pulsed mode or in a continuous mode. The skin may optionally be actively cooled, without contacting the skin. This method may also be used for tightening the skin and for remodeling collagen tissue in the subcutaneous tissue. With the applicator not touching the skin, the need for cooling the skin and bio-compatibility factors is avoided. There is also a lower risk of overheating the skin, and there is no need to continuously move the applicator.

Methods are provided for selectively heating human skin and maintaining the desired elements of human skin at predetermined temperature with minimal need of personnel assistance during therapy.

DETAILED DESCRIPTION

Methods and apparatus for focused remodeling and downsizing the volume of subcutaneous lipid-rich cells, body contouring and tightening skin tissue, without contact with the skin, have now been invented. Prior art methods generally require direct contact of an applicator onto the skin. This in turn typically also requires use of active skin cooling elements. Direct skin contact can also raise bio-compatibility issues with the applicator material and further requires high sanitary standards, since the applicators are used for treatment of different patients. The practitioner must also be skilled in using the applicators since there is a risk of burning the patient.

These disadvantages are overcome by transmitting electromagnetic energy into the subcutaneous tissue, without physical contact with the patient. Contactless application enables simultaneous treatments of large areas of human body. In the present contactless methods, the skin may be sufficiently cooled passively by circulating air.

An air gap or material with high air permeability may be placed between the skin and the applicator. This arrangement uses the human thermoregulatory system for cooling and avoids the need of artificial cooling of the skin. The human thermoregulatory system enables perspiration and other bodily fluids to evaporate and cool the surrounding skin. Additionally to enhance evaporation, airflow circulation between patient's skin and the applicator may be increased using a stream of chilled or room temperature air. Use of cooling fluids and gels is not necessary. This reduces costs and increases patient comfort. The applicator may be in direct or indirect contact with patient's skin.

Airflow can be provided between the applicator and the skin by positioning an air mover close to the skin. The air mover may be attached to or made part of the applicator. The air mover may be a fan, ventilator, blower or vacuum. The air mover may be provided as an air tube connected to air source for moving air through the air tube to the patient's skin. The air source can alternatively cooled to provide chilled air.

With the applicator applying heat over a larger area, constant movement of the applicator is not needed. The applicator may remain in a stationery position relative to the patient for several seconds or longer, for example, for at least 10, 30, 60, 120 or 240 seconds, or longer.

The increase of the temperature in the dermal and the sub dermal tissues also affects the triple-helix structure of collagen fibers contained in such tissues. This may result in remodeling and rejuvenation of collagen, increase of skin density and dermal thickening based on neocollagenesis. Skin tightening may also be achieved.

Remodeling and reducing the volume of subcutaneous lipid-rich cells, and skin tightening in the targeted areas, can change the overall appearance of the body, for use in body contouring, body reshaping and cellulite treatment.

In one aspect, the present methods work on the principle of selective deep heating of the human tissue containing low volume of water, such as adipose tissue. Radiant energy may be provided to the skin by one or more capacitive electrodes generating an electromagnetic field. Electrode polarity may continuously fluctuate and induce an electromagnetic field inside tissue. Selective heating in the skin occurs due to dielectric losses. An inductive electrode may alternatively be used.

The treatment system for creating the electromagnetic field can use bipolar electrodes, where electrodes alternates between active and return function and where the thermal gradient beneath electrodes is during treatment almost the same. The system may alternatively use monopolar electrodes, where the return electrode has sufficiently large area in contact with skin of patient and is typically positioned a relative larger distance from the active electrode. A unipolar electrode may also optionally be used.

The electromagnetic field can be applied in continuous or pulse mode. In a continuous application mode, the electromagnetic field is applied continuously, which provides a maximum amount of heating. Using a pulse mode, the heat is local and typically limited to about 400 W. With the pulse mode, a high frequency field is applied in short intervals (typically (50-2000 μs) and on various pulse frequencies (typically 50 to 1500 Hz). The maximum output with the continuous method is typically limited to 200 W.

Electromagnetic energy is provided through the skin to the underlying dermal and/or sub dermal tissue, without contacting the skin. The radiant energy is converted into heat in the sub dermal tissue. The radiant energy enables focused heating of the subcutaneous adipose tissue and sub dermal collagen tissue, leading to accelerating lipolysis and adipocyte apoptosis. At the same time the triple helix structure of collagen fibers may result in remodeling and/or rejuvenation of collagen, increase of skin density and dermal thickening based on neocollagenesis. Subcutaneous lipid-rich cells may be remodeled and/or reduced in volume, contouring and tightening skin tissue.

Figure 1:
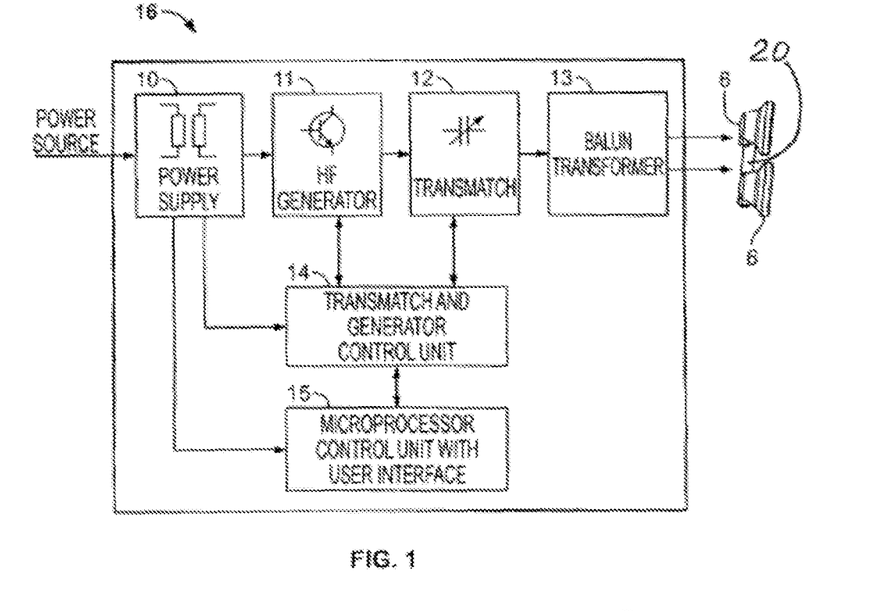
FIG. 1 is a schematic diagram of a system for controlled deep heating of sub dermal tissues.

Referring now to FIG. 1, a system 16 applies electromagnetic energy through a skin layer, such as the epidermis, and to the underlying dermal and/or sub dermal tissue, and underlying collagen tissue, causing acceleration of lipolysis and collagen remodeling. The system may include 6 blocks. The power supply 10 is connected to a power source. An HF generator (high frequency generator) 11 and a transmatch and generator control unit 14, and a microprocessor control unit with user interface 15, are connected to the power supply 10. The HF generator 11 may generate an electromagnetic field at 13.56 or 40.68 or 27.12 MHz, or 2.45 GHz or optionally at other frequencies as well. The 13.56, 27.12 and 40.68 MHz and 2.45 GHz frequencies avoid creating radio interference, as these frequencies are exclusively assigned as free or open frequencies.

The microprocessor control unit with user interface 15 provides communication between the transmatch and generator control unit 14 and user interface, which may be a touch screen on the device display.

The transmatch and generator control unit 14 receives information from the operator via the control unit and regulates the operation of the HF generator 11 and the transmatch 12. The transmatch transmits HF to a balun transformer 13, which converts unbalanced impedance to balanced impedance. This processed signal goes to two capacitive applicators 6, which may be positioned 0.5 cm or higher above the surface of the skin or applied on dielectric or insulating, non-conductive material which is in contact with the skin surface.

Figure 2:
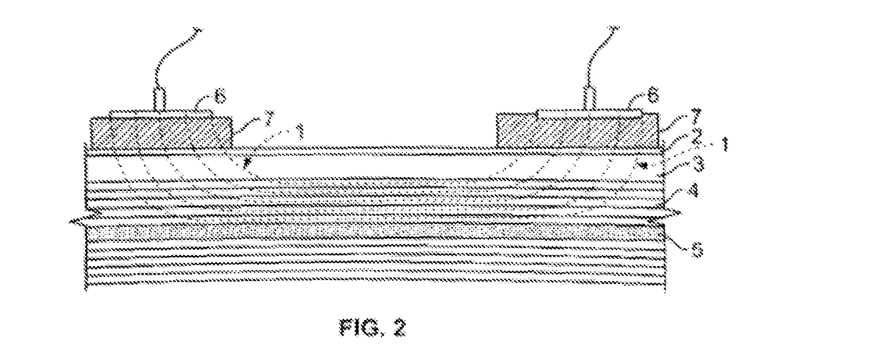
FIG. 2 is a schematic view of a trans-regional course of electromagnetic field.

FIG. 2 is a schematic representation of a heat distribution under the skin. One or more applicators 6 create an electromagnetic field. This electromagnetic field crosses through the skin 2, subcutaneous fat 3 and muscle 4 or the bone 5. Capacitive applicators 6 provide deep heating, which heats selectively only structures with low volume, of water. A spacer 7 such as a towel, gauze pad, foam pad, cloth pad and another porous or air permeable materials may be placed on the skin, with the applicator then placed on top of the spacer 7. The spacer may be made from three-dimensional material with high air permeability formed by two square fabrics with preferably low square densities connected by tough filaments. This automatically sets the separation distance between the applicator and the skin, and prevents the applicator from touching the skin. The spacer 7 may be made of various dielectric or electrically non-conductive materials. The spacer 7 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

A selective heating process is observed in the dermis 3 due to dielectric losses of induced electromagnetic field. Dielectric loss is created, as part of an AC electromagnetic field power is converted to heat in the dielectric. During this process, ions accelerate and collide, polar molecules rotate, non-polar molecules undergo distortion and these movements produce thermal energy. Skin and muscle, are largely not affected by electromagnetic field 1 as they contain water and the blood, circulation provides for cooling. Bone 5 gets little if any heating because the applicators 6 are positioned to create a field only on the upper structures. The lipid cells of the adipose tissue contain less water than the surrounding tissue and are therefore heated at higher level than the surrounding tissue.

Electrodes can be placed coplanar, tilted to each other or parallel to each other. Coplanar electrodes can be advantageously (but not exclusively) used for heating the shallow layers of human skin. In this arrangement the electromagnetic waves tend to travel through materials with the lowest impedance, such as epidermis and dermis. This effect may be favorably used for remodeling subcutaneous collagen and elastin fibers.

Electrodes tilted to each other can be advantageously used for different sized patients, limbs or another body parts. Electrodes parallel to each other can be advantageously (but not exclusively) used for heating adipose tissue. In this arrangement adipose fat tissue acts as sub cutis layer with highest impedance and therefore transforms most of induced electromagnetic energy to heat.

In coplanar or tilted arrangement of electrodes, more distance between electrodes induces more energy in deep tissues of patient's skin, which is desirable for subcutaneous adipose tissue heating. The electrodes may be used one by one in one plane distanced at least 6 cm. This can be obtained by distribution of electrodes in predetermined minimal distance or by a matrix or array of electrodes that are switched so that adjoining electrodes are not powered on at the same time. Therefore, a specified minimal distance between electrodes will be maintained. Shorter distances between electrodes may be advantageous for treatment of shallow layers of patient's skin.

Figure 3:
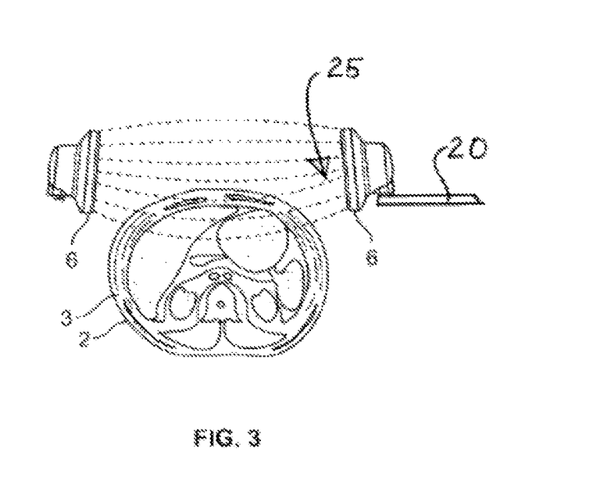
FIGS. 3 and 4 are schematic examples of positioning of electrodes shown in FIG. 1.
Figure 4:
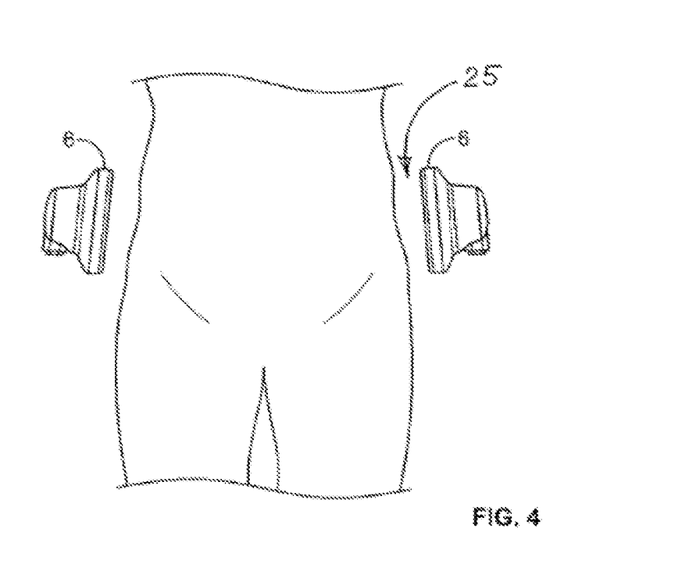

FIGS. 3 and 4 are schematic examples of positioning of the applicators or electrodes 6 providing radiant energy through the skin 2 to subcutaneous fat 3. The applicator includes one or more electrodes and wiring connections to system components. The electrodes are positioned approximately 2-3 cm above the surface of the skin and separated from the skin by an air gap, or placed onto a spacer 7 which is in contact with the skin surface, as shown in FIG. 2. The spacer 7, if used, may correspondingly typically be about 0.5 to 1 cm thick. The applicator 6 may be temporarily fixed in position relative to the patient, if desired, for example on a mechanical fixture or holder. It is not necessary in each instance for the applicator to be continuously moving during the procedure. This makes the procedure easier to perform, since user need not constantly keep moving the applicator over the patient's skin. Consequently, the user can accordingly simultaneously attend to other needs of a patient. The applicator 6 may have a relatively large surface area, so that the field 1 is distributed more widely through the subcutaneous tissue. For example, the applicator may have a surface area of at least about 15, 30, 50, 100, or 150 square centimeters.

If more than one applicator is used, applicators may be positioned on opposite sides of the patient. A spacer may be positioned between one or more applicator and the skin of the patient. The electromagnetic waves may be transmitted in the range of 13.553-13.567 or 26.957-27.283 or 40.66-40.70 MHz or 2.4-2.5 GHz from the applicator into the subcutaneous tissue. The temperature of the skin surface may be increased to about 32-45° C.

One or more of the applicators may have a temperature sensor which measures and monitors the temperature of the treated tissue. Temperature can be analyzed by a microprocessor control unit. The temperature sensor may be a contactless sensor (e.g. infrared temperature sensor), contact sensor (e.g. resistance temperature detector) or invasive sensor (e.g. a thermocouple) for exact temperature measuring of deep or shallow tissue of human skin. The microprocessor controller may use algorithms to calculate the deep or shallow temperature based on the surface temperature of the skin. A feedback system may be used to measure and control temperatures on the skin surface or below the skin surface. The feedback system may control the temperature to a predetermined level, for example by adjusting power, airflow circulation, phase shifting, supplemental magnetic field, and perhaps other parameters, or combinations of them.

Figure 5:
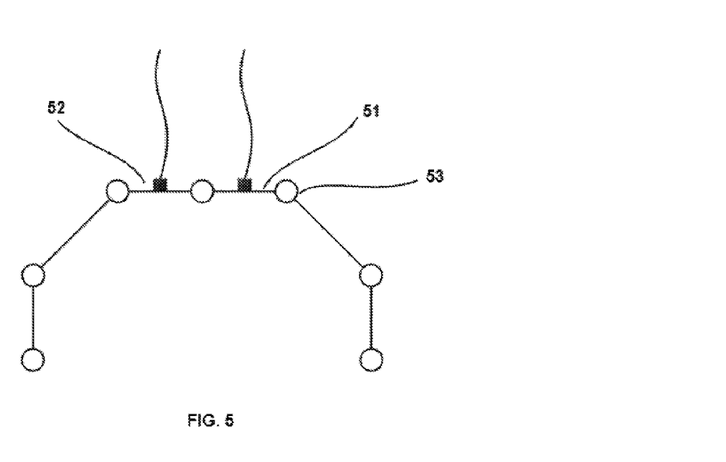
FIG. 5 is schematic diagram of an alternative electrode design.

FIG. 5 illustrates arrangement of a mechanical fixture or holder for tilting electrodes which enables treatment of different sized patients, limbs or other body parts. A tilting device may include at least two electrodes 51, 52 connected by joints 53, allowing the electrodes to be spatially adjustable. Each electrode may further enable connection of additional electrodes, so that the applicator can be extended according to the needs of the particular patient. The joint connection with additional electrode(s) may be a plug and play device. The microprocessor control unit may be programmed to recognize the additional electrodes and allow the user to select a therapy with regard to the number of participating electrodes. In some embodiments the radiofrequency device also enables shifting of electrodes for example by parallelogram or simply by fastening of each electrode on mechanical fixture or holder. In another embodiment the arrangement of mechanical fixture or holder enables tilting and shifting of electrodes.

Substantially coplanar electrodes may be advantageous for treatment of deep tissue of patient's skin. Coplanar electrodes or electrodes tilted towards each other may be used with a low impedance material placed between the electrode/s and skin of patient. The low impedance material may be laid on patient's skin. Shallow layers of patient skin may overheat during treatment with large amount of energy because the electromagnetic field tends to travel through tissue with the lowest impedance. Supplemental low impedance material can improve the energy flow so that a relatively large amount of energy can be safely transmitted into the tissue. The material with low impedance may be a metal, alloys or other material with the same or lower impedance than epidermis and dermis.

Figure 6:
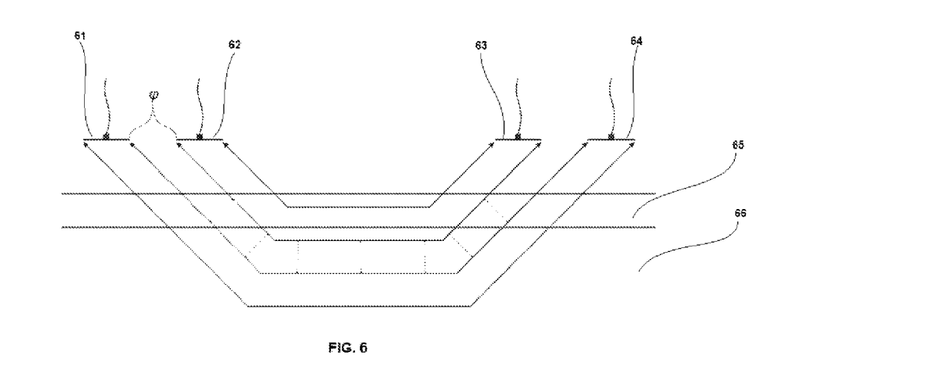
FIG. 6 is schematic diagram of induced currents inside tissue.

FIG. 6 shows an alternative design having phase controlled radiofrequency signals which may be used to improve targeting of induced electromagnetic energy into a predetermined depth of tissue. This system may include two or more pairs of electrodes, where the first pair of electrodes 62 and 63 is inside the second pair of electrodes 61 and 64. Electrode polarity between electrodes of the inner first pair fluctuates relative to the outer second pair with phase shift.

In the coplanar or tilted arrangement of electrodes, a shallow layer of the skin 65 such as epidermis and dermis is heated more when the electrodes are close together. A deep layer of the skin 66 such as hypodermis is heated more with increasing distance between the electrodes.

As the distances between electrodes of each pair are different, each pair induces an electromagnetic field at different depths of tissue. In a coplanar or tilted arrangement of electrodes, a greater distance between the electrodes induces greater energy in deep tissues of patient's skin. With the phase shift of these pairs it is possible to control the shape of induced electromagnetic energy and therefore heating of targeted tissue.

In FIG. 6, the induced electromagnetic field is represented by solid line arrows, with dashed line arrows representing induced movement of charged particles caused by phase shift of induced electromagnetic fields.

Phase shift can be used in array of electrodes, where each electrode is shifted in phase separately. With phase shift it is possible to decrease the difference of potentials of adjoining electrodes and therefore decrease the amount of induced electromagnetic field in shallow layers of skin. Even if the electrodes are close together phase shift may reduce unwanted heating or overheating in shallow layers of skin. Phase shifting may be used in a method for skin treatment by positioning first and second electrodes adjacent to the skin of the patient, with the electrodes not touching the skin, and providing airflow circulation between the electrodes and the skin. The electrodes transmit radio frequency waves into the skin, with the radio frequency waves heating the skin. The first electrode may transmit radio frequency waves having a phase different from the radio frequency waves transmitted by the second electrode.

Figure 7:
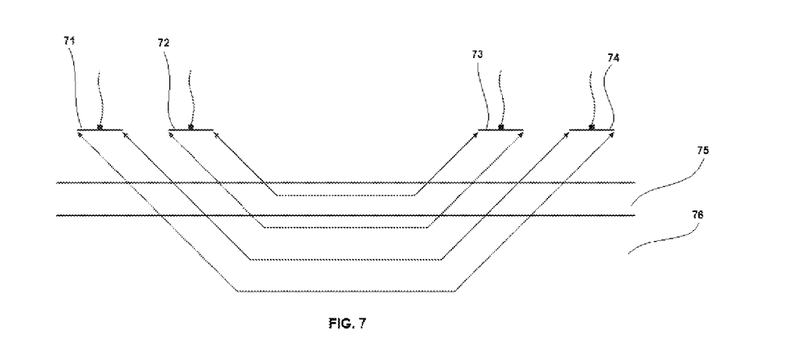
FIG. 7 is schematic diagram of induced currents inside tissue without use of an external magnetic field.
Figure 8:
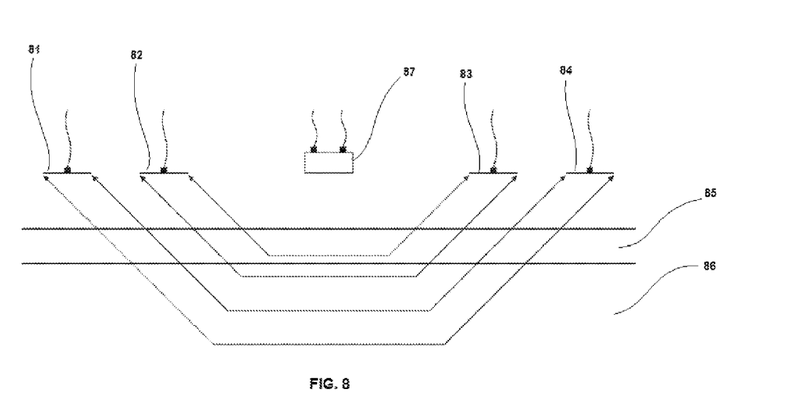
FIG. 8 is schematic diagram of induced currents inside tissue with use of external magnetic field.

Another system for providing targeted electromagnetic energy may use a supplemental magnetic field. FIG. 7 illustrates induced electromagnetic field inside the tissue without a supplemental magnetic field. The inner electrode pair of electrodes 72 and 73 induces an electromagnetic filed mainly inside a shallow layer of the skin 75. The outer electrode pair 71 and 74 induces an electromagnetic filed mainly in a deeper layer of the skin 76. FIG. 8 illustrates an induced electromagnetic field trajectory influenced by a permanent magnetic material or an inducing magnetic field from an electromagnet 87. The inner electrode pair of electrodes 82 and 83 induces an electromagnetic filed which is shifted from a shallow layer of the skin 85 more into a deeper layer of the skin 86. The outer electrode pair 81 and 84 induces an electromagnetic field mainly in the deeper layer of the skin 86.

An induced electromagnetic field can be deflected towards or away from the upper layers or lower layers of skin, depending on type of therapy. Based on the temperature of the skin, the microprocessor control unit can regulate the electromagnet to change the magnetic field and therefore influence the depth of the induced electromagnetic field in the skin of patient.

Figure 9:
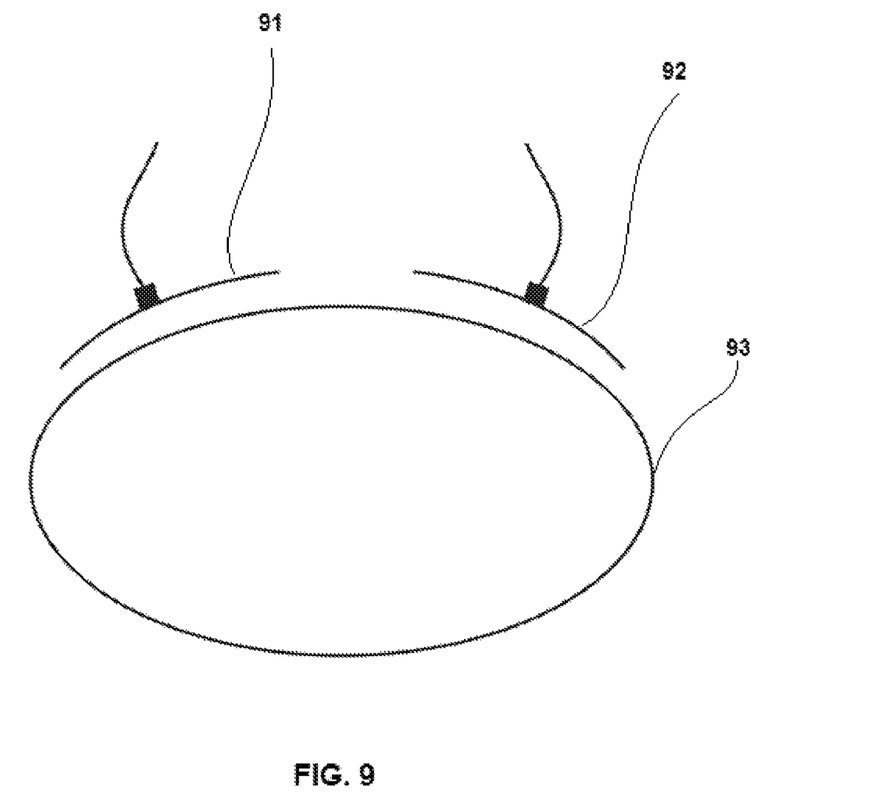
FIG. 9 is schematic diagram of a flexible electrode arrangement in transverse cross-section.

FIG. 9 illustrates a treatment system having malleable/flexible electrodes 91 and 92. In this design the applicator can be shaped according to the patient's shape to better match the individual. The distance between skin of the patient and applicator is therefore constant and heating of tissue is homogenous. This may help to eliminate possible temperature differences which might occur if there are any shape irregularities on human skin. Such a flexible applicator may be created from bipolar, monopolar or even unipolar system and one or more electrodes. The electrode(s) may be made of flexible material to insure that the electrode(s) are the same distance from the patient's skin and substantially parallel with skin of patient.

Systems and methods may provide improved skin surface treatment for large area sections and body parts with minimal need of personnel assistance during therapy. As shown in FIG. 7, a plurality of electrodes may be are arranged adjacent to each other. The electrodes may be interconnected and partially separated from each other by a carrier surface. If the electrodes are made of rigid material the distance between these individual carrier surfaces provide high flexibility of treatment area. Alternatively, the electrodes may be a flexible material. The electrodes may be selectively switched on and off during treatment, optionally with the electrodes switched so that adjoining electrodes will not be powered on at the same time.

Figure 10:
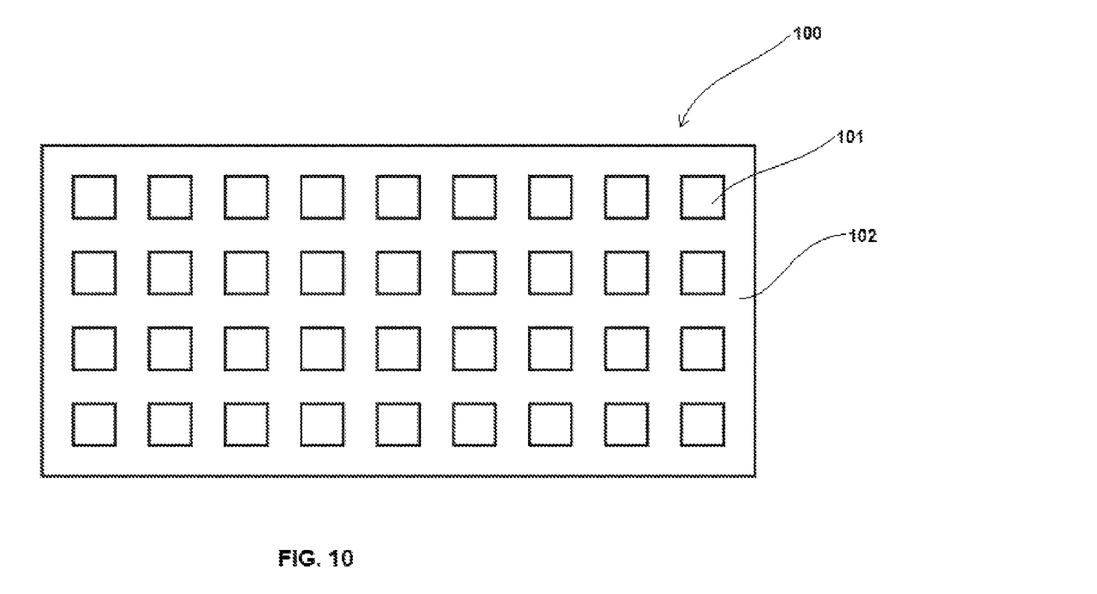
FIG. 10 is schematic diagram of arrangement of electrodes into a matrix.

As shown in FIG. 10, a system is provided for treating large areas or parts of the body 100 with minimal need of personnel assistance during therapy. Multiple electrodes 101 may be arranged adjacent to each other, with the electrode interconnected and partially separated from each other by carrier surface 102. If the electrodes are made of rigid material the spacing between the electrodes allows for flexible positioning of the electrodes on the body 100. However, preferably the electrodes are made from flexible material. The electrodes can be selectively switched on and off during treatment, optionally in a way so that adjoining electrodes are not powered on at the same time. This switching, if used, may be controlled by the microprocessor control unit and be set by the user in a user interface, or it may be set automatically based on treatment type.

Other forms of switching, such as random switching, or other algorithm switching of electrodes at specified electrode locations or distances, may also be use, to provide treatment to various depths.

The present system for skin treatment may be provided with an array of electrodes adjacent to the skin of the patient, with the electrodes not in contact with the skin of the patient. A microprocessor control unit is electrically connected, directly or indirectly, to the electrodes, with the electrodes transmitting radio frequency waves and the microprocessor selectively switching electrodes in the array on and off, optionally in a way so that adjoining electrodes are not powered on at the same time. A fixture may be used for holding the electrodes in a fixed position relative to the skin during at least part of the treatment process. The electrodes may be uniformly spaced apart into rows and columns, or aligned on concentric circles, or randomly arranged. The electrodes can be separated from the skin by an air gap or a spacer. The electrodes may be flexible, to conform to the skin or to a spacer, or to allow for greater versatility in positioning the electrodes. Temperature feedback control may be used to control skin temperature. Airflow may be provided between an electrode and the skin by positioning an air mover adjacent to the skin, for example using an air mover attached to the electrode or applicator, or an air tube connected to air source for moving air through the air tube to the patient's skin. The system may also be adapted to expose tissue to a supplemental magnetic field.

Thus, novel methods and systems have been shown and described. Various modifications and substitutions may be made without departing from the spirit and scope of the invention. The invention, therefore, should not be limited, except by the following claims and their equivalents.

The invention claimed is:

1. A method for treating a patient, comprising:
providing a high frequency generator, a transmatch, and an applicator including at least one capacitive electrode, the applicator having a surface area of at least 15 cm²;
processing a signal from the high frequency generator via the transmatch;
providing the processed signal to the applicator;
positioning the applicator adjacent to skin of the patient, with the capacitive electrode separated from the skin of the patient by a spacer;
transmitting radio frequency waves from the applicator through the skin of the patient;
cooling of the skin of the patient using a stream of chilled air or room temperature air provided between the applicator and the skin of the patient; and
heating a tissue of the patient and maintaining the tissue of the patient at 32-45° C. via the radio frequency waves.

2. The method of claim 1 further including providing a balun transformer and processing a signal from the high frequency generator via the transmatch and the balun transformer.

3. The method of claim 1 wherein the tissue heated includes abdomen.

4. The method of claim 1 with the patient having a volume of lipid-rich cells and further including remodeling and/or downsizing the volume of lipid-rich cells via the heating.

5. The method of claim 1 with the applicator remaining in a stationary position during at least 10 seconds.

6. The method of claim 1, further comprising a mechanical holder which keeps the applicator in fixed position during at least part of treatment process.

7. The method of claim 1 further including exposing the patient to a supplemental magnetic field.

8. The method of claim 1 with the applicator including at least one flexible electrode and further including shaping the flexible electrode based on a shape of the patient.

9. A method for treating a patient, comprising:
providing a high frequency generator, a transmatch, and an applicator including at least one capacitive electrode, the applicator having a surface area of at least 15 cm²;
processing a signal from the high frequency generator via the transmatch;
providing the processed signal to the applicator;
positioning the applicator adjacent to skin of the patient, with the capacitive electrode separated from the skin of the patient by a spacer;
transmitting radio frequency waves from the applicator through the skin of the patient;
moving air between the applicator and the skin by vacuum; and
heating a tissue of the patient and maintaining the tissue of the patient at 32-45° C. via the radio frequency waves.

10. The method of claim 9 further including providing a balun transformer and processing a signal from the high frequency generator via the transmatch and the balun transformer.

11. The method of claim 10 further comprising a generator control unit which regulates the operation of the HF generator and the transmatch.

12. The method of claim 9 wherein the tissue heated includes the abdomen.

13. The method of claim 9 the tissue of the patient having a volume of lipid-rich cells, and further comprising remodeling and/or downsizing the volume of lipid-rich cells via the heating.

14. The method of claim 13, wherein subcutaneous tissue is heated to 40° C. or more.

15. The method of claim 9 further including cooling of the patient's skin.

16. The method of claim 15 wherein the air is a stream of chilled or room temperature air.

17. The method of claim 9 further including exposing the patient to a supplemental magnetic field.

18. The method of claim 9 with the applicator including at least one flexible electrode and further including shaping the flexible electrode based on a shape of the patient.

* * * * *